(12) United States Patent
Schütze et al.

(10) Patent No.: US 8,431,078 B2
(45) Date of Patent: Apr. 30, 2013

(54) SAMPLE HOLDER FOR A RECEPTION DEVICE RECEIVING BIOLOGICAL OBJECTS AND MICROSCOPE SYSTEM DESIGNED TO OPERATE USING ONE SUCH SAMPLE HOLDER

(75) Inventors: Karin Schütze, Tutzing (DE); Raimund Schütze, Tutzing (DE); Hendrik Herrmann, Haunsholen (DE)

(73) Assignee: Carl Zeiss Microscopy GmbH (DE)

( * ) Notice: Subject to any disclaimer, the term of this patent is extended or adjusted under 35 U.S.C. 154(b) by 1639 days.

(21) Appl. No.: 10/535,762

(22) PCT Filed: Nov. 20, 2003

(86) PCT No.: PCT/EP03/13013
§ 371 (c)(1),
(2), (4) Date: Jul. 22, 2005

(87) PCT Pub. No.: WO2004/045768
PCT Pub. Date: Jun. 3, 2004

(65) Prior Publication Data
US 2006/0012773 A1 Jan. 19, 2006

(30) Foreign Application Priority Data
Nov. 20, 2002 (DE) .................................. 102 54 229

(51) Int. Cl.
*G01N 21/01* (2006.01)
*G01N 1/00* (2006.01)

(52) U.S. Cl.
USPC .................. 422/50; 356/36; 356/244; 435/4; 435/40.5; 435/283.1; 435/40.52; 435/873

(58) Field of Classification Search .................. 422/104, 422/50; 435/4, 40.5, 283.1, 40.52, 9.68, 435/873; 356/36, 244
See application file for complete search history.

(56) References Cited

U.S. PATENT DOCUMENTS

| | | | | |
|---|---|---|---|---|
| 2,914,746 A | * | 11/1959 | James | 525/382 |
| 5,216,932 A | | 6/1993 | Takei | |
| 5,592,289 A | * | 1/1997 | Norris | 356/244 |
| 5,998,129 A | * | 12/1999 | Schutze et al. | 435/4 |
| 6,152,662 A | * | 11/2000 | Titus et al. | 409/132 |
| 6,258,326 B1 | | 7/2001 | Modlin | |
| 6,673,315 B2 | * | 1/2004 | Sheridan et al. | 422/50 |
| 6,787,301 B2 | * | 9/2004 | Ganser et al. | 435/4 |
| 2002/0056345 A1 | | 5/2002 | Ganser et al. | |
| 2002/0155617 A1 | | 10/2002 | Harootunian | |

FOREIGN PATENT DOCUMENTS

| | | |
|---|---|---|
| DE | 41 39 423 A1 | 11/1991 |
| DE | 101 52 404 A1 | 10/2001 |

(Continued)

*Primary Examiner* — Vickie Kim
*Assistant Examiner* — Rebecca M Fritchman
(74) *Attorney, Agent, or Firm* — Mayback & Hoffman, P.A.; Gregory L. Mayback; Rebecca A. Tie (57) ABSTRACT

A sample container (20) for receptacle devices for receiving biological objects that may be used for example as collecting devices (30) in laser microdissection systems is described, in which the sample container (20) has a coding (23) with the aid of which the sample holder in the laser microdissection system can be unambiguously identified in order subsequently to be able to allocate correctly biological objects (43) to be dissected to individual receptacle containers (31) of the identified receptacle device (30) or of the identified sample holder (20), so as to carry out a fully automated microdissection procedure.

21 Claims, 3 Drawing Sheets

FOREIGN PATENT DOCUMENTS

| WO | WO 97/29355 | 8/1997 |
| WO | WO 99/39176 A | 8/1999 |
| WO | WO 01/60519 A1 | 8/2001 |
| WO | WO 01/73398 A1 | 10/2001 |

* cited by examiner

SAMPLE HOLDER FOR A RECEPTION DEVICE RECEIVING BIOLOGICAL OBJECTS AND MICROSCOPE SYSTEM DESIGNED TO OPERATE USING ONE SUCH SAMPLE HOLDER

The present invention relates to a holder for a receptacle device for receiving biological objects, in which the receptacle device may in turn comprise one or more receptacle containers for receiving the biological objects. In addition the present invention relates to a microscope system that is designed for operation with such a holder or with such a receptacle device. In particular the present invention relates to a microscope system designed as a laser microdissection system, in which the holder is designed to hold a device for collecting biological objects dissected from a biological material with the aid of the laser microdissection system.

Laser microdissection systems are used for the processing, separation and/or obtaining of microscopically small biological objects. Such a conventional laser microdissection system of the applicants is described for example in WO 97/29355 A1 or WO 01/73398 A1. Using the laser microdissection systems disclosed in these specifications, individual biological objects that are arranged on a two-dimensional object carrier can be selected in a computer-assisted manner and treated with a laser beam. In this connection a selected object may be at least partly separated from the surrounding material, for example with the aid of the laser beam, in order then to catapult the object from the object carrier to a collecting device by means of a laser-induced transport process with the aid of a laser shot that is targeted on the biological object. A glass object carrier on which a polymer membrane with the biological material to be processed is clamped may for example be used as object carrier. The use of membrane-only preparations is also possible.

The process described above enables biological objects to be separated, graded and obtained, wherein in the context of the present invention patent application the expression "biological objects" is understood to denote all living or fixed biological cells or cell constituents that are a constituent part of a liquid or solid biological material, such as for example a cell tissue, a smear or a cell culture, etc. With the aid of the aforedescribed process the in each case selected biological objects can be selectively loaded with a chosen substance by contactless laser microinjection, following which the successfully injected biological objects can be sorted. The biological objects may be mounted next to one another on the object carrier, whereby the aforedescribed processing operation can be carried out quickly and in a contactless manner. The survival capability and morphology of the biological objects is in this connection guaranteed, i.e. the biological objects are not damaged or harmed by the microinjection procedure and by the separation and catapulting process.

In principle the laser-induced transport process described above, i.e. the catapulting of individual, previously selected biological objects from the in each case surrounding biological material, may also be carried out without prior free preparation of the in each case selected biological object if the laser energy and/or the laser focal point at the moment when the separate laser shot is fired is/are selected so that the resultant impulse of this laser shot is sufficient to dislodge the corresponding biological object from the surrounding mass and to transport the object to the collecting device.

Since it is relatively complicated to carry out manually the method described hereinbefore with the desired precision, the laser microdissection systems are normally designed to be computer-assisted, i.e. the excision and/or catapulting of a selected object, the so-called dissection, is carried out in a computer-assisted manner, which means that the laser light source that generates the laser beam serving for the dissection and/or catapulting is automatically manipulated and the relative movement between the laser beam and the object carrier containing the biological material necessary for the dissection and/or catapulting is automatically generated and controlled. In particular, a computer-assisted selection and/or marking of the desired biological objects situated on the object carrier is possible, so that these may subsequently be processed automatically with the laser microdissection system. The laser microdissection system includes for this purpose a screen or monitor, on which is displayed a video image, recorded by a digital camera, of the biological material situated on the object carrier. The user can then trace a desired dissection outline on the screen or video image with the aid of suitable graphics tools, which is then automatically simulated with the laser beam in a computer-assisted manner in order to excise the thereby selected biological object. In a similar way and manner a desired biological object that is to be catapulted out can also be marked on the screen or on the video image, the separate laser impulse or laser shot then being fired at the desired site on the biological material.

Although with the known laser microdissection systems described above a computer-assisted and automated processing of the biological material located on the object carrier is in principle already possible, there is a basic need for a microdissection process that can be implemented in a fully automated manner. This relates not only to laser microdissection systems, but to microscope systems in general, in which an investigation or processing of biological objects is to be carried out in as fully automated a manner as possible.

The object of the present invention is accordingly to provide a possible way of improving an automatic processing and/or investigation of biological objects with the aid of a microscope system, in particular a laser microdissection system, that permits a fully automated observation and/or processing of biological objects with the aid of such microscope systems.

This object is achieved according to the invention by a holder for a receptacle device for receiving biological objects having the features of claim 1, and a microscope system designed for operation with such a holder or with such a receptacle device, having the features of claim 11. The subclaims define in each case preferred and advantageous embodiments of the present invention.

According to the invention a holder is proposed for a receptacle device that is provided for receiving one or more biological objects, wherein the holder is designed in such a way that, when used in a microscope system, it holds the receptacle device in the microscope system in a suitable way and means for observing and/or processing with the aid of the microscope system. In this connection the holder has a coding by means of which the holder and/or the receptacle device held thereby can be unambiguously identified. In particular the coding may be such that different types of receptacle devices and/or holders can be distinguished with the aid of the said coding.

The coding may in this connection be devised so that it can be scanned optically as well as inductively or capacitatively. The receptacle device held by the holder may in principle be a receptacle device of any suitable type with one or more receptacle containers for receiving biological objects. In particular the receptacle device may include caps of Eppendorf containers, tubes of Eppendorf containers, strips or matrix-like arrangements (arrays) of such caps or tubes, ciphergenic chips, wafers or microtitre plates, etc.

The microscope system proposed according to the invention comprises identification means for identifying a receptacle device held by a holder according to the invention by evaluating the corresponding coding, and control means for the automatic adjustment, specific to the receptacle device, of at least one function of the microscope system depending on the identified receptacle device. This function of the microscope system specific to the receptacle device may for example be the automatic representation of a diagrammatic image of the identified receptacle device on a reproduction equipment of the microscope, so that a user can then specifically select for the identified receptacle device individual receptacle containers for an observation or processing with the microscope system and can then selectively proceed with the observation or processing.

The microscope system according to the invention is preferably a laser microdissection system, in which biological objects of a biological material arranged on an object carrier can be selectively dissected with the aid of a laser beam and conveyed to the receptacle device. As has been described hereinbefore, this may in particular be effected by directing individual laser shots onto the biological objects to be dissected, in order to catapult the selected biological objects into desired receptacle containers of the identified receptacle device. After the laser microdissection system has identified the holder that is used and the receptacle device held thereby, an image of the identified receptacle device can be shown on a reproduction equipment, whereby a user can then specify in a computer-assisted manner which biological objects of the biological material located on the object carrier are to be conveyed to which receptacle containers of the identified receptacle device. This may be carried out for example with the aid of a processing list that is established in a computer-assisted manner by the respective user, as is described and disclosed in DE 101 52 404 A1 in the name of the applicants, to which specification in its entirety reference is specifically made.

Preferably the laser microdissection system is also designed in such a way that after a dissection procedure with the aid of the laser microdissection system, the imaging means that is in any case provided in the laser microdissection system is driven over the identified receptacle device in order to generate one or more general images of the receptacle device with the dissectates (dissected material) situated therein, which can then be shown on the reproduction equipment so that the quality of the dissection can be assessed by evaluating the displayed general images. For this purpose it is also helpful if the laser microdissection system automatically prepares a dissection protocol depending on the identified receptacle device.

Fully automated microdissection processes can be carried out on the basis of the automatic recognition of employed holders and/or receptacle devices that is realised according to the invention. The software parameters of the corresponding laser microdissection systems can easily be adapted to incorporate further holders and/or receptacle devices. Operational errors can be avoided and the workflow can be accelerated. Furthermore a standardisation and good reproducibility of each procedure is ensured.

The invention can be combined particularly advantageously with the list-type summary already described hereinbefore of biological objects to be processed, wherein by grouping the desired objects, for example depending on their type, a fully automated processing and, in the case of a laser microdissection system, gathering and collection of the desired dissectates in the receptacle containers of the identified receptacle device can be achieved without complicated replacement of the receptacle devices and/or the receptacle containers included therein. The microscope system recognises automatically the collecting device used in each case, for example a microtitre plate, and responds with a corresponding automated function workflow, which can lead from a corresponding screen structure via the allocation of selected biological objects to individual receptacle containers of the identified receptacle device up to the automated and computer-assisted manipulation of the desired receptacle container of the identified receptacle device.

The invention is not restricted to the use in laser microdissection systems, but may in principle also be applied to holders for receptacle devices that may be used in automated and/or computer-assisted microscope systems.

The present invention is described in more detail hereinafter with the aid of preferred examples of implementation and with reference to the accompanying drawings, in which.

Figure 1:
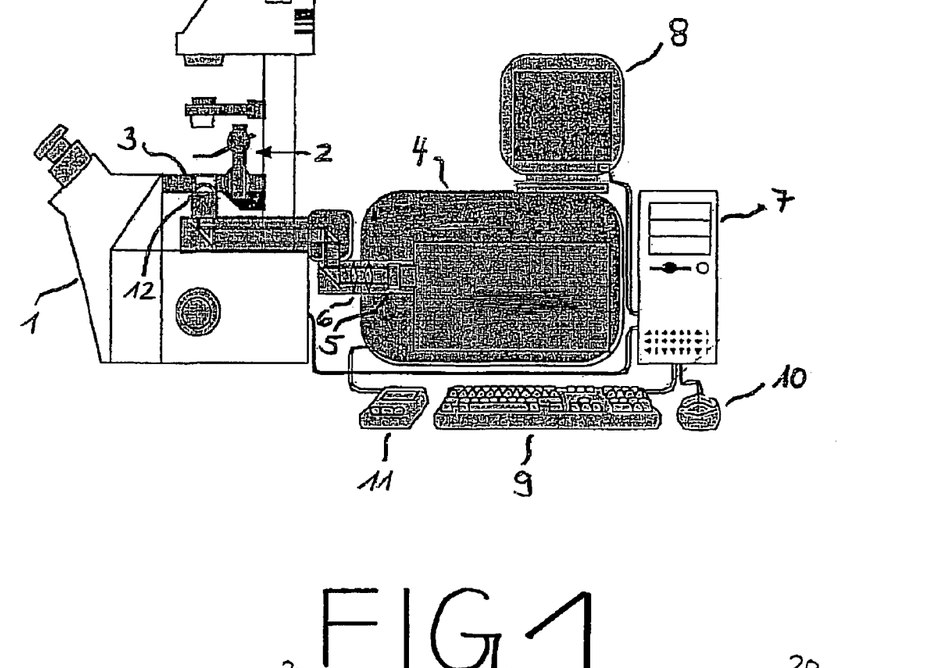
FIG. 1 shows the arrangement of a laser microdissection system according to a preferred example of implementation of the present invention.

The laser microdissection system shown in FIG. 1 comprises a laser device 4 with a laser light source for generating a laser beam. Furthermore a lens system 6 is installed in the laser device 4, via which the laser beam can be coupled into a microscope 1 and the laser focal point in the object plane can be matched to the optical focal point of the microscope 1. The laser light source may for example be a pulsed UV nitrogen laser.

For the precise adjustment of the laser energy a quartz filter 5 is arranged perpendicular to the laser beam path, which can be manually or also automatically adjusted for the setting of the laser energy. In addition to the setting of the laser energy the laser focal point can also be adjusted independently of the microscope focal point, i.e. the focal point of the laser beam can be displaced in the z direction relative to the object plane of the microscope 1, wherein for this purpose the lenses 6 shown in FIG. 1 may be manually or automatically adjusted.

The laser beam is coupled by a plurality of coated beam splitters into the microscope 1 and deflected onto a lens 12. The diameter of the laser beam incident on the object plane depends decisively on the numerical aperture of the lens 12.

The laser beam emitted via the lens 12 finally strikes a motor-driven and computer-controlled microscope table or carrier table 3, on which is arranged an object carrier with a biological material to be processed. A motor-driven and computer-controlled adjustment device 2, which is also termed a manipulator, is situated above the carrier table 3. The carrier table 3 can preferably by driven in the x direction and y direction, although in principle an adjustment in the z direction is also conceivable. A needle or micropipette for the microinjection of biological objects may be mounted on the adjustment device 2. Within the scope of the present invention it is assumed however that a collecting device is mounted on the adjustment device 2 in order to capture biological objects catapulted from the object carrier. The motor-driven adjustment device 2 may be driven in a computer-assisted manner in the x/y direction as well as in the z direction.

The microscope 1 may be a microscope of any suitable specification. The laser microdissection system illustrated in FIG. 1 has an inverse construction, in which the laser beam strikes the object carrier from underneath in order to catapult biological objects located thereon upwards onto the collecting device, which is not shown in FIG. 1. In the case of a normal arrangement however the laser beam strikes the object carrier from above, so that biological objects excised from the biological material fall downwards onto the collecting device situated underneath the object carrier.

The microscope 1 is equipped with a video camera, in particular a CCD (Charge Coupled Device) video camera, which records in particular the region of the object carrier above the lens 12. The video signal from this video camera is passed to a conventional commercial computer 7 and is processed there so that the corresponding video image can be displayed in real time on a screen or a monitor 8 of the computer 7. Likewise, a storage of individual video images on a suitable storage medium of the computer 7 is possible. In addition an analogue or digital video recorder for recording the video images supplied by the video camera may also be coupled to the computer 7.

As is described in more detail hereinafter, various functions are implemented on the computer 7 and/or by the software operating therewith that permits a computer-assisted, i.e. automated, manipulation of the laser device 4 as well as the microscope 1, so that for example the laser can be automatically activated and the adjustment device 2 and/or the carrier table 3 can be automatically driven. Similarly, these computer-assisted functions permit a particularly user-friendly selection and processing of desired biological objects of the biological material located on the object carrier. Conventional input means, such as for example a keyboard 9 or a computer mouse 10, are provided for the adjustment and/or selection of these functions. In addition a foot-actuated switch 11 may be associated with the laser device 4, by means of which the laser can be manually activated.

FIG. 2A shows a receptacle device 30—in the illustrated example in the form of a microtitre plate with a plurality of depressions, so-called "wells"—which is provided for use in the laser microdissection system illustrated in FIG. 1. The receptacle device 30 is in this connection held by a surrounding frame 21 of a holder 20, in which an attachment 22 with comb-like projections 23 projects from one side of the frame 21. This attachment 22 serves on the one hand to secure or mount the holder 20 together with the receptacle device 30 on the adjustment device 2 shown in FIG. 1. On the other hand the comb-like projections 23 of this attachment 22 serve as a coding, which identifies the type of holder 20 and the receptacle device. 30 held thereby. The receptacle device 30 may simply be placed in the frame 21 of the holder 20 or alternatively may also be clamped therein. The receptacle containers 31 of the receptacle device 30 formed as wells serve to receive the dissectates excised by means of the laser beam from the biological material located on the object carrier.

Figure 5:
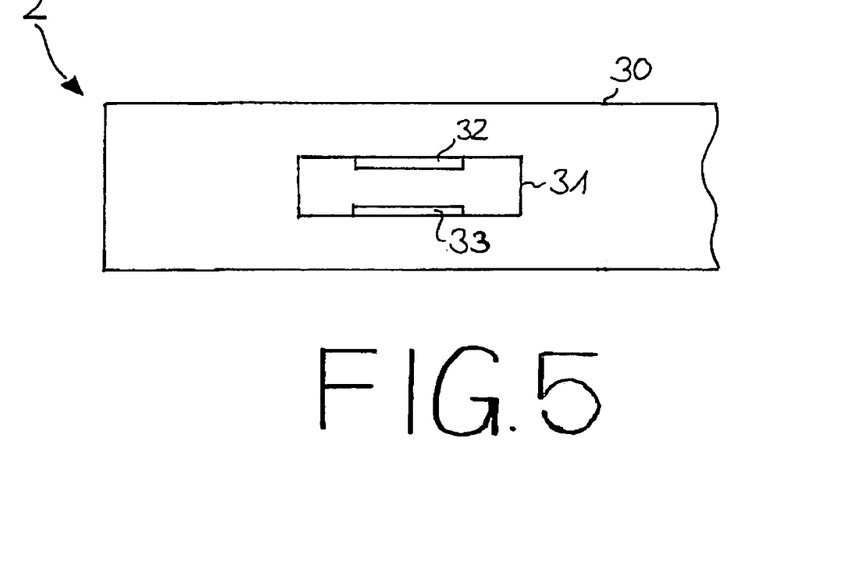
FIG. 5 is a diagrammatic view of an arm of an adjustment device of a laser microdissection system according to the invention, in which this arm is designed to be coupled to a holder according to the invention.

FIG. 5 illustrates by way of example an arm 30 of the adjustment device 2 shown in FIG. 1. The arm 30 has a receiver 31, into which the attachment 22 of the holder 20 is to be inserted. A strip-like or matrix-like arrangement 32 with light sources, for example light-emitting diodes, is arranged in the region of this receiver 31, a corresponding arrangement 33 with photodiodes being provided opposite this arrangement 32. The light sources of the arrangement 32 emit light beams, which are received by the photodiodes of the arrangement 33 and converted into electrical signals. Depending on the arrangement of the comb-like projections 23 of the attachment 22 of the holder 20 used in each case, individual numbers of these light beams are either interrupted or allowed to pass, so that depending on the electrical signals generated by the individual photodiodes of the arrangement 33, by comparing the signal pattern with a predetermined signal pattern stored in the computer 7 information can be obtained as regards the type of holder 20 and/or the receptacle device 30 held thereby. Obviously other possibilities for the optical scanning of the coding formed by the comb-like projections 23 are also possible. Thus for example image detection means may be provided, which record an image of the comb-like projections so that the computer 7 and/or the software implemented thereby can automatically determine the type of holder 20 that is used and/or the type of receptacle device 30 that is used.

A strip with a plurality of Eppendorf container caps used therein as receptacle containers 31 is illustrated in FIG. 2B as an example of a receptacle device 30.

In this case too the attachment 22 mounted on the frame 21 comprises comb-like projections as coding, which as can be seen differ as regards their design and arrangement from the comb-like projections illustrated in FIG. 2A, so that by evaluating these comb-like projections a clear distinction can be made between the two receptacle devices 30.

Figure 3:
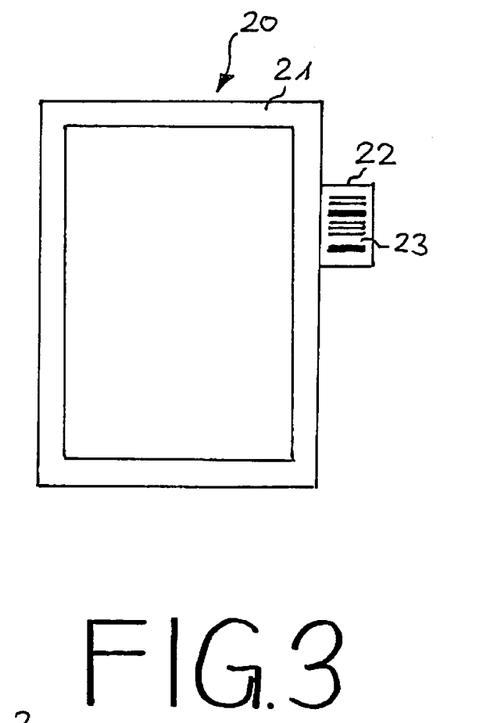
FIG. 3 shows a holder according to an example of implementation of the present invention with an optically scannable coding in the form of a barcode.

FIG. 3 shows a further example of an optically scannable coding, in which a barcode is applied as coding 23 to the attachment 22 illustrated in this figure.

Figure 4:
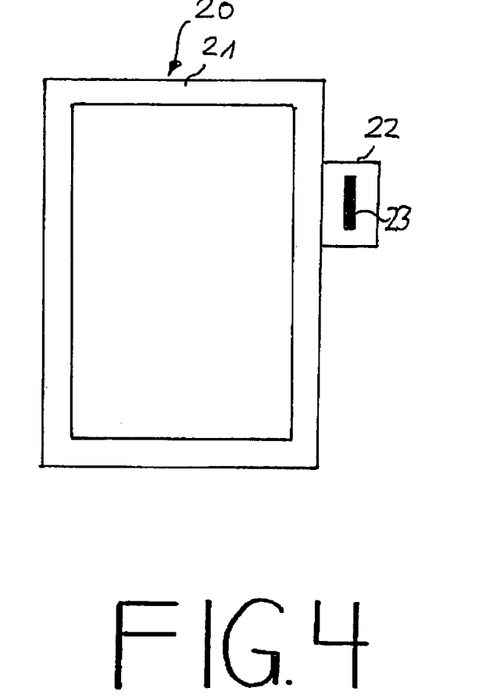
FIG. 4 shows a holder according to an example of implementation of the present invention with a coding in the form of a capacitative or inductive transponder.

Obviously the present invention is not restricted to optically scannable codings, but may in principle be used for all types of coding. The use of inductive or capacitative transponders is particularly advantageous, which as shown in FIG. 4 may be integrated as coding 23 in the attachment 22, whereby these transponders when inserted for example into the receptacle 31 shown in FIG. 5 can alter in a defined manner an electromagnetic field generated therein, in order to obtain from the resultant change of the electromagnetic field information on the type of holder 20 that is used or type of receptacle device that is used.

In principle the coding may be provided at any suitable place on the holder 20 or also directly on the receptacle device 30. The holder 20 and the receptacle device may also be formed in one part. Likewise, it is conceivable to combine different coding possibilities with one another in order to achieve an absolute recognition of each of the available holders or various receptacle devices. For example, apart from the conventional holders for the laser microdissection there may also be mentioned holders that comprise various MALDI (Matrix-Assisted Laser Desorption Ionisation) boards or different SELDI (Surface-Enhanced Laser Desorption Ionisation) carriers, which are coded as such but are structurally identical (internal coding by suitable secondary measures for recognition purposes).

The basic operation of the laser microdissection system illustrated in FIG. 1 with a holder or a receptacle device of the type described hereinbefore is as follows.

Figure 2:
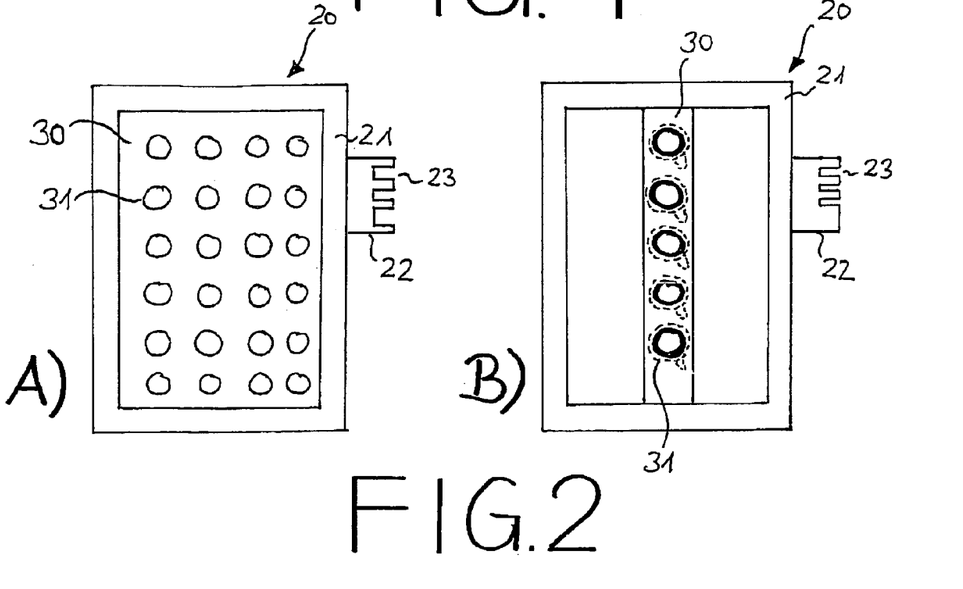
FIG. 2A and FIG. 2B show holders according to an example of implementation of the present invention with an optically scannable coding in the form of comb-like projections.
Figure 6:
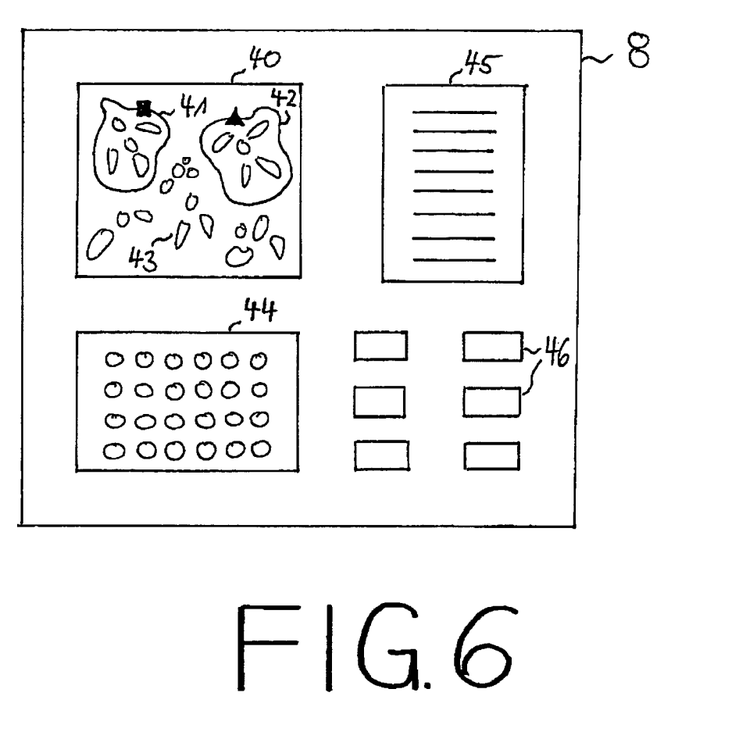
FIG. 6 shows in simplified form a screen structure of a laser microdissection system according to the invention.

After placing a desired receptacle device 30 by means of the corresponding holder 20 on the adjustment device 2 of the laser microdissection system, the holder 20 that is used and the receptacle device 30 that is used are automatically identified as described above, and the computer 7 reacts to the identified receptacle device with a corresponding screen display, as is illustrated by way of example in FIG. 6.

As is clear from FIG. 6, the video image of the biological material located on the object carrier and which contains a large number of biological objects 43 is displayed by the software of the computer 7 on the screen 8 in a first screen region or window 40. A diagrammatic representation of the identified receptacle device is displayed in a second screen section or window 44, wherein in the case of the example of implementation illustrated in FIG. 6 it is assumed that the identified receptacle device is a microtitre plate with a number of wells, illustrated in FIG. 6, as receptacle containers for the biological objects 43 to be dissected. A list of the type discussed in the printed specification DE 101 52 404.8 A1 described hereinbefore is illustrated in a further screen section or window 45, with the aid of which list a user can allocate individual selected biological objects 43 to desired receptacle containers of the identified receptacle device. In addition various control keys or software functions 46 are illustrated in FIG. 6, by means of which a user may for example store, delete or transfer a list that has already been prepared, or start a microdissection procedure, etc.

The user of the laser microdissection system can now mark in the screen section 40 with the aid of graphics tools of the software of the laser microdissection system individual biological objects 43 to be processed, as is illustrated by way of example in FIG. 6 with the aid of demarcation lines 41 and 42 that have been drawn round the desired biological objects. As is disclosed in the aforedescribed printed specification, it can be specified for each biological object to be processed how the operation should be performed, i.e. it may for example be decided whether it is to be simply excised and then catapulted out with a separate laser shot, or is simply to be catapulted directly by firing an individual laser shot. The type of processing can be specified for each selected biological object in the list 45. In addition the selected biological objects can be combined into groups with the aid of the list 45, in which a combination according to object groups or markings/colour is possible. In other words, all biological objects identified by a certain colour or a certain marking, for example a square or a triangle as shown in FIG. 6, are in each case *combined in one group. The total number of combined selected biological objects in a group as well as their total surface area is preferably also specified in the list 45 for each group. The list 45 may be stored as described hereinbefore, in which preferably for each previously selected biological object contained in the list the position with reference to a previously selected reference position of the respective biological material is also stored in order to ensure that if an object carrier with the already previously investigated biological material is reused, then the biological objects that have been selected and marked there can be correctly manipulated and positioned.

Each individual element or biological object of the list 45 may preferably be processed separately with the laser beam with the aid of the control buttons 46. In addition it is obviously also possible to process the biological objects contained in the list 45 in groups, i.e. the biological objects combined in one group by the user are then automatically moved by the automatic manipulation of the laser device 4 as well as of the carrier table or microscope table 3, in order to convey them to desired receptacle containers 31 of the receptacle device 30 held by the adjustment device 2 with the aid of the holder 20.

The combination of selected biological objects in groups is in particular advantageous for processing biological objects of the same type in groups and possibly for catapulting them into a common receptacle container or into a joint group of receptacle containers. If for example tumour cells are to be placed in one receptacle container and healthy cells in another receptacle container, then it is recommended to mark the desired cells or biological objects on the screen section 40 in such a way that the demarcation lines of the tumour cells are drawn in a first colour or with a first marking, and the demarcation lines of the healthy cells are drawn in a second colour or with a second marking. The tumour cells and the healthy cells would then appear in each case combined in separate groups in the list 45, so that all tumour cells could then be treated as a group with the laser beam and—depending on the laser function adjusted in each case—catapulted into the desired receptacle containers. The healthy cells could then be collected in separate receptacle containers.

The representation of the receptacle device identified by the software of the laser microdissection system in the screen section 44 is particularly advantageous since it enables the user to make a correct allocation of the biological objects 43 to be processed to the individual available receptacle containers of the identified receptacle device 30. For each biological object to be processed according to the list displayed in the screen section 45, the user specifies with the aid of corresponding software functions into which receptacle containers 31 of the identified receptacle device 30 the desired biological object is to be transported. Obviously it is also possible in this way to allocate as described above individual selected biological objects to a common receptacle container, in order for example to collect all healthy cells in a first receptacle container and all tumour cells in a second receptacle container, etc. The allocation of the selected biological objects to the available receptacle containers may for example easily be achieved by clicking onto and thereby selecting with the computer mouse 10 for each selected biological object the desired receptacle container 31 of the identified receptacle device 30 when preparing the list 45. An allocation of several selected biological objects of the list 45 to a common receptacle container may likewise be achieved in this way.

The automatic identification of the receptacle device that is used as well as the display of a corresponding diagrammatic image of the identified receptacle device in the screen section 44 ensures that operating errors are avoided, since the user is automatically notified of the receptacle device that is used, whereby depending on the identified receptacle device only the receptacle containers with the correct arrangement in the screen section 44 that have been allocated to this identified receptacle device are offered to the user for the microdissection, so that overall the workflow sequence can be speeded up.

After the user has specified the allocation of the selected biological objects to the desired receptacle containers 31 of the identified receptacle device 30, the user can then start the automatic microdissection procedure by actuating a corresponding button 46, whereby for the biological objects contained in the list 45 and that have previously been selected the in each case desired processing is carried out by corresponding manipulation of the laser device 4 as well as of the carrier table 3. After the desired receptacle container 31 of the identified receptacle device 30 has also been specified for each selected biological object in the list 45, the adjustment device 2 on which the holder 20 together with the corresponding receptacle device 30 is located is at the same time manipulated in such a way by the software of the laser microdissection system for each biological object to be processed that in each case the receptacle container associated with the biological object to be processed is automatically moved over the laser beam in order to be able to convey the desired biological object to the desired receptacle container. This work sequence takes place fully automatically, so that all biological objects included in the list 45 can be deposited in the associated receptacle containers without any further intervention by the user.

If such a microdissection procedure has been carried out, the software of the laser microdissection system removes the processed receptacle containers 31 with the video camera integrated in the microscope 1 or with the aid of other image recording devices, in order to generate general images of the receptacle containers 31 with the aid of a navigator function and display them on the screen 8 of the laser microdissection system. The user thus has the possibility of judging the quality of the dissection procedure that has been carried out by evaluating these general images.

Similarly, a general dissection protocol is then automatically prepared by the software of the laser microdissection system, which provides detailed information on the data of the dissection procedure and contains for example statistical data as well as information on the list 45 with the allocations of the dissectates to the individual receptacle containers and on the constellations of the dissectates contained in the individual receptacle containers, etc. This general dissection protocol is in turn prepared in particular depending on the type of identified receptacle device.

In principle the user can decide between a manual operation and an automatic operation, in which differences may arise depending on the identified receptacle device.

In a manual operation the user directly manipulates the individual desired biological objects or the corresponding receptacle containers, whereby in the case of a scanned procedure a manual or automatic post-adjustment may optionally be effected by manipulating the carrier table 3 or the adjustment device 2. With a free manual procedure it is also possible to finely adjust manually individual receptacle containers 31 of the receptacle device 30 that is used, so that the user can view the corresponding receptacle containers and execute fine movements on the latter for example in order to rediscover catapulted dissectates.

The use of the list 45 described hereinbefore in combination with the automatic identification of the receptacle device that is used allows for example in a particularly advantageous manner the fully automated execution of concentration steps that can be employed for example in subsequent investigations in a clinical calibration procedure. Thus for example a specified concentration procedure can be carried out in different receptacle containers (in FIG. 6 for example in the receptacle containers in the left-hand column of the identified receptacle device) beginning with one biological object up to a specified number of biological objects, in order to collect different concentrations of dissectates in the individual allocated receptacle containers.

For the sake of completeness it may also be mentioned here that the navigator function described hereinbefore, by means of which the receptacle containers 31 that are used are "scanned" after a dissection procedure, can be carried out merely for one used receptacle container as well as for a group or a whole area of used receptacle containers, in which the general images taken with the aid of this navigator function are for example displayed using a high magnification lens, for example 100× or 63× magnification, by arranging the individual general images in adjacent rows on the screen 8 of the laser microdissection system. The general images together with the general dissection protocol, in which the selected biological objects together with the desired receptacle containers are listed, may be stored for quality assurance and documentation purposes. It is particularly advantageous if all used receptacle containers 31, i.e. all receptacle containers to which dissectates were conveyed, are automatically "scanned" with the aid of the aforedescribed navigator function after a dissection procedure.

The invention claimed is:

1. A laser microdissection system with a microscope for observing a biological material located on an object carrier, the system comprising:
    a laser device for excising a biological object from the biological material by means of laser radiation; and
    at least one holder containing a receptacle device having a plurality of receptacle containers, each receptacle container provided for receiving the biological object excised from the biological material, for operation with the laser microdissection system, wherein:
    the at least one holder has a coding that identifies the type of receptacle device; and
    identification means are provided for identifying the receptacle device held in each case by the holder by evaluating the coding of the holder, and control means are provided and are designed in such a way that, depending on the receptacle device identified in each case, the control means displays a diagrammatic representation of the identified receptacle device on a display to provide information about the receptacle device to a user and provides selection functions specific to the receptacle device that allow a user to control the allocation of individual biological objects to be excised from the biological material to individual receptacle containers of the receptacle device identified in each case.

2. Laser microdissection system according to claim 1, wherein the identification means are designed for the optical scanning of the coding of the holder.

3. Laser microdissection system according to claim 1, wherein the identification means are designed for the inductive scanning of the coding of the holder.

4. Laser microdissection system according to claim 1, wherein the identification means are designed for the capacitative scanning of the coding of the holder.

5. Laser microdissection system according to claim 1, wherein the control means are designed in such a way that, depending on the identified receptacle device, they form an image of the identified receptacle device on a reproduction device.

6. Laser microdissection system according to claim 1, wherein the control means are designed in such a way that, depending on the identified receptacle device, they provide selection functions specific to the receptacle device for the automatic manipulation of the receptacle device.

7. Laser microdissection system according to claim 1, wherein the control means are designed in such a way that, depending on the identified receptacle device, they manipulate in a manner specific to the receptacle device an adjustment device of the microscope system to which the holder is to be coupled, in order to position the receptacle device in the microscope system with the aid of the adjustment device.

8. Laser microdissection system according claim 1, wherein image recording means for recording an image of the receptacle device are provided, and whereby the control means are designed in such a way that, depending on the identified receptacle device, they manipulate the image recording means in a manner specific to the receptacle device in such away that these automatically remove the receptacle device in order to record an image of the receptacle device.

9. Laser microdissection system according to claim 8, wherein the control means are designed in such a way that after a dissection procedure they automatically manipulate the image recording means in order to record the image of the receptacle device at least in a region of those receptacle containers in which the biological objects are dissected.

10. Laser microdissection system according to claim 1, wherein the control means are designed in such a way that, depending on the identified receptacle device, they prepare in a manner specific to the receptacle device a dissection protocol for a dissection work sequence carried out with respect to the receptacle device.

11. Laser microdissection system according to claim 1, wherein the holder comprises a frame for holding the receptacle device.

12. Laser microdissection system according to claim 1, wherein the coding is an optically scannable coding.

13. Laser microdissection system according to claim 12, wherein the coding comprises comb-like projections that extend from the holder, whereby the receptacle device is identified by the arrangement of the projections.

14. Laser microdissection system according to claim 12 wherein the coding comprises a barcode.

15. Laser microdissection system according to claim 1, wherein the coding comprises an inductive coding.

16. Laser microdissection system according to claim 1, wherein the coding comprises a capacitative coding.

17. Laser microdissection system according to claim 15, wherein the coding comprises a transponder.

18. Laser microdissection system according to claim 1, wherein the holder is designed to hold a receptacle device that is selected from a group comprising a cap, a tube, a microtitre plate and arrangements thereof.

19. A laser microdissection system with a microscope for observing a biological material located on an object carrier, the system comprising:
   a laser device for excising a biological object from the biological material by means of laser radiation; and
   at least one holder containing a receptacle device having a plurality of receptacle containers, each receptacle container provided for receiving the biological object excised from the biological material, for operation with the laser microdissection system, wherein:
      the at least one holder has a coding that identifies the type of receptacle device; and
      a receptacle identifier for identifying the receptacle device held in each case by the holder by evaluating the coding of the holder, and a controller, depending on the receptacle device identified in each case, the controller displaying a diagrammatic representation of the identified receptacle device on display to provide information about the receptacle device to a user and providing selection functions specific to the receptacle device that allow a user to control the allocation of individual biological objects to be excised from the biological material to individual receptacle containers of the receptacle device identified in each case.

20. A laser microdissection system for use with a microscope for observing a biological material located on an object carrier, the system comprising:
   a laser radiation excising device for excising a biological object from the biological material with laser radiation;
   a multi-receptacle device having a plurality of receptacle containers, each of the receptacle containers shaped to receive the biological object excised from the biological material, the multi-receptacle device having at least one type;
   at least one multi-receptacle holder shaped to hold the multi-receptacle device thereat and having an identification coding for ascertaining the type of the multi-receptacle device;
   a coding evaluator operable to identify the multi-receptacle device held by the multi-receptacle holder dependent upon the respective identification coding; and
   a controller operable to, depending on the multi-receptacle device respectively identified, display a diagrammatic representation of the identified multi-receptacle device on display to provide information about the receptacle device to
   a user and provide selection functions specific to the multi-receptacle device that allow a user to control the allocation of individual biological objects excised from the biological material to individual ones of the plurality of receptacle containers.

21. A laser microdissection system with a microscope for observing a biological material located on an object carrier, the system comprising:
   a laser device for excising a biological object from the biological material by means of laser radiation; and
   at least one holder containing a receptacle device having a plurality of receptacle containers, each receptacle container shaped for receiving the biological object excised from the biological material, for operation with the laser microdissection system, wherein:
      the at least one holder has a coding that identifies the type of receptacle device;
      identification means are provided for identifying the receptacle device held in each case by the holder by evaluating the coding of the holder, and control means are provided and are designed in such a way that, depending on the receptacle device identified in each case, the control means provides information about the receptacle device that is displayed to a user and provides selection functions specific to the receptacle device that allow a user to control the allocation of individual biological objects to be excised from the biological material to individual receptacle containers of the receptacle device identified in each case; and
      image recording means for recording an image of the receptacle device are provided, whereby the control means control the image recording means in a manner specific to the receptacle device to record an image of the receptacle device with said individual biological objects excised and contained in the respectively allocated receptacle containers.

\* \* \* \* \*

UNITED STATES PATENT AND TRADEMARK OFFICE
CERTIFICATE OF CORRECTION

PATENT NO. : 8,431,078 B2
APPLICATION NO. : 10/535762
DATED : April 30, 2013
INVENTOR(S) : Karin Schutze et al.

It is certified that error appears in the above-identified patent and that said Letters Patent is hereby corrected as shown below:

In the Specification

At column 2, line 42, delete "having the features of claim 1,"

At column 2, line 44, delete "having the features of claim 11"; and

At column 2, lines 44-46, delete "The sub-claims define in each case preferred and advantageous embodiments of the present invention."

Signed and Sealed this
Nineteenth Day of November, 2013

Teresa Stanek Rea
*Deputy Director of the United States Patent and Trademark Office*